(12) United States Patent
McBride et al.

(10) Patent No.: US 9,220,539 B2
(45) Date of Patent: Dec. 29, 2015

(54) SPINAL IMPLANT SYSTEM AND METHOD

(75) Inventors: Larry McBride, Memphis, TN (US);
Jeff Justis, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 590 days.

(21) Appl. No.: 13/424,048

(22) Filed: Mar. 19, 2012

(65) Prior Publication Data
US 2013/0245705 A1 Sep. 19, 2013

(51) Int. Cl.
*A61B 17/56* (2006.01)
*A61B 17/70* (2006.01)

(52) U.S. Cl.
CPC ............ *A61B 17/7032* (2013.01); *A61B 17/708* (2013.01); *A61B 17/7076* (2013.01)

(58) Field of Classification Search
CPC ........... A61B 17/7032; A61B 17/7056; A61B 17/708; A61B 17/7082; A61B 17/7083; A61B 17/7085
USPC .......... 606/300–321, 99, 104, 250, 246, 86 A
See application file for complete search history.

(56) References Cited

U.S. PATENT DOCUMENTS

| | | | |
|---|---|---|---|
| 3,963,028 A | 6/1976 | Cooley et al. | |
| 5,336,170 A | 8/1994 | Salerno et al. | |
| 5,891,145 A | 4/1999 | Morrison et al. | |
| 6,648,888 B1 * | 11/2003 | Shluzas .................... | 606/86 A |
| 7,226,413 B2 | 6/2007 | McKinley | |
| 7,476,240 B2 | 1/2009 | Raymond | |
| 7,491,208 B2 * | 2/2009 | Pond et al. .................... | 606/104 |
| 7,491,218 B2 | 2/2009 | Landry et al. | |
| 7,563,264 B2 | 7/2009 | Landry et al. | |
| 7,575,581 B2 | 8/2009 | Lovell | |
| 7,666,189 B2 * | 2/2010 | Gerber et al. ................ | 606/104 |
| 7,794,464 B2 | 9/2010 | Bridwell et al. | |
| 7,802,574 B2 | 9/2010 | Schultz | |
| 7,824,411 B2 * | 11/2010 | Varieur et al. .............. | 606/86 A |
| 7,842,044 B2 | 11/2010 | Runco et al. | |
| 7,846,093 B2 | 12/2010 | Gorek et al. | |
| 7,854,751 B2 | 12/2010 | Sicvol et al. | |
| 7,887,541 B2 | 2/2011 | Runco et al. | |
| 7,914,558 B2 | 3/2011 | Landry et al. | |
| 7,918,857 B2 | 4/2011 | Dziedzic et al. | |
| 7,918,858 B2 | 4/2011 | Stad et al. | |
| 7,922,746 B2 | 4/2011 | Miller | |
| 7,927,334 B2 | 4/2011 | Miller et al. | |
| 7,985,242 B2 | 7/2011 | Forton et al. | |
| 8,012,141 B2 | 9/2011 | Wright et al. | |
| 8,096,996 B2 | 1/2012 | Gutierrez et al. | |

(Continued)

FOREIGN PATENT DOCUMENTS

WO   WO 2010103198 A1 *  9/2010  ............. A61B 17/70

*Primary Examiner* — Zade Coley

(57) ABSTRACT

An extender includes a first arm defining a first longitudinal axis and including a first extension and a second extension. The first extension includes an outer surface and a projection extending from the outer surface, the projection including a ramp and a first locking element. The first extension includes an inner surface defining a longitudinal cavity. The projection is transversely moveable between a first configuration such that the projection extends beyond the outer surface and a second configuration whereby the second extension axially translates within the longitudinal cavity and engages the ramp such that the projection is disposed in alignment with the outer surface and the first locking element engages an implant. Methods of use are disclosed.

18 Claims, 18 Drawing Sheets

(56) References Cited

U.S. PATENT DOCUMENTS

| | | |
|---|---|---|
| 8,439,922 B1* | 5/2013 | Arnold et al. ............... 606/86 A |
| 8,439,924 B1* | 5/2013 | McBride et al. ............ 606/86 A |
| 8,603,094 B2* | 12/2013 | Walker et al. ............... 606/86 A |
| 2004/0138662 A1* | 7/2004 | Landry et al. ................... 606/61 |
| 2006/0036255 A1* | 2/2006 | Pond et al. ....................... 606/86 |
| 2006/0074418 A1 | 4/2006 | Jackson |
| 2006/0079903 A1 | 4/2006 | Wong |
| 2006/0111712 A1 | 5/2006 | Jackson |
| 2006/0111715 A1 | 5/2006 | Jackson |
| 2006/0111730 A1 | 5/2006 | Hay |
| 2006/0122597 A1* | 6/2006 | Jones et al. ..................... 606/61 |
| 2006/0264962 A1 | 11/2006 | Chin et al. |
| 2006/0293680 A1 | 12/2006 | Jackson |
| 2007/0213714 A1 | 9/2007 | Justis |
| 2007/0244493 A1 | 10/2007 | Bjerken |
| 2007/0270867 A1 | 11/2007 | Miller et al. |
| 2008/0015601 A1 | 1/2008 | Castro et al. |
| 2008/0172062 A1 | 7/2008 | Donahue et al. |
| 2008/0234678 A1 | 9/2008 | Gutierrez et al. |
| 2008/0243190 A1 | 10/2008 | Dziedzic et al. |
| 2008/0319477 A1* | 12/2008 | Justis et al. ................... 606/232 |
| 2009/0105771 A1 | 4/2009 | Lei et al. |
| 2009/0143828 A1 | 6/2009 | Stad et al. |
| 2009/0157125 A1 | 6/2009 | Hoffman et al. |
| 2009/0171391 A1* | 7/2009 | Hutton et al. ................. 606/246 |
| 2009/0222046 A1 | 9/2009 | Gorek |
| 2009/0228053 A1* | 9/2009 | Kolb et al. ................... 606/86 A |
| 2009/0228054 A1 | 9/2009 | Hoffman et al. |
| 2009/0228055 A1 | 9/2009 | Jackson |
| 2009/0228056 A1 | 9/2009 | Jackson |
| 2009/0234395 A1 | 9/2009 | Hoffman et al. |
| 2009/0264895 A1 | 10/2009 | Gasperut et al. |
| 2009/0318972 A1 | 12/2009 | Jackson |
| 2010/0030283 A1 | 2/2010 | King |
| 2010/0036443 A1 | 2/2010 | Hutton et al. |
| 2010/0063552 A1 | 3/2010 | Chin et al. |
| 2010/0069972 A1 | 3/2010 | Jones et al. |
| 2010/0198268 A1 | 8/2010 | Zhang et al. |
| 2010/0198271 A1 | 8/2010 | Leone |
| 2010/0312279 A1 | 12/2010 | Gephart et al. |
| 2011/0015678 A1 | 1/2011 | Jackson |
| 2011/0022088 A1 | 1/2011 | Forton et al. |
| 2011/0106178 A1 | 5/2011 | Schwab |
| 2011/0202096 A1 | 8/2011 | White et al. |
| 2011/0218581 A1* | 9/2011 | Justis ........................... 606/86 A |
| 2011/0263945 A1* | 10/2011 | Peterson et al. ............. 600/213 |
| 2011/0264098 A1 | 10/2011 | Cobbs |
| 2012/0253402 A1* | 10/2012 | McLean ....................... 606/264 |
| 2013/0103094 A1* | 4/2013 | Beale et al. ................... 606/279 |

* cited by examiner

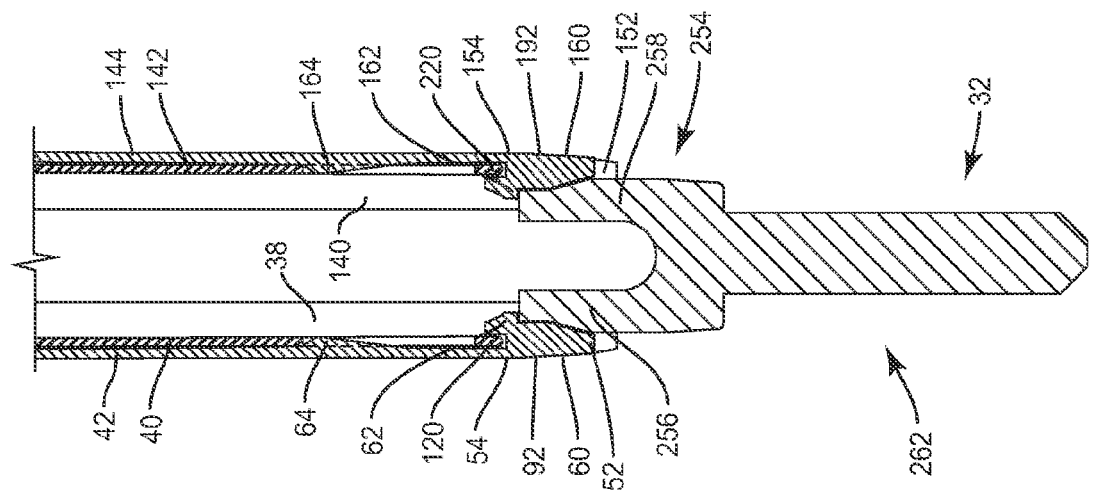
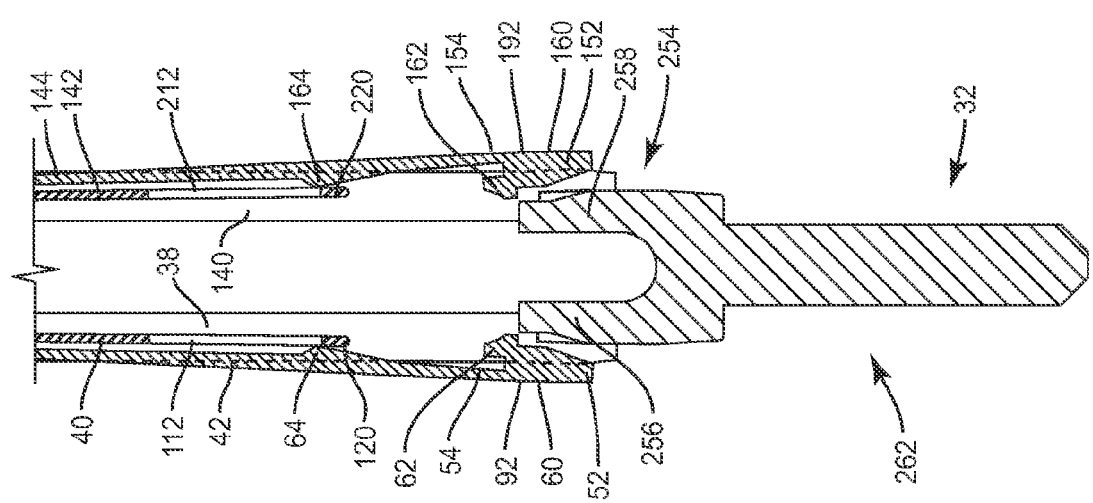

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, an extender is provided. The extender includes a first arm defining a first longitudinal axis, a first extension and a second extension. The first extension includes an outer surface and a projection extending from the outer surface. The projection includes a ramp and a first locking element. The first extension includes an inner surface defining a longitudinal cavity. The projection is transversely moveable between a first configuration, such that the projection extends beyond the outer surface, and a second configuration whereby the second extension axially translates within the longitudinal cavity and engages the ramp such that the projection is disposed in alignment with the outer surface and the first locking element engages an implant.

In one embodiment, in accordance with the principles of the present disclosure, a spinal implant system is provided. The spinal implant system includes an extender and a bone fastener. The extender has a first arm and a second arm. The first arm defines a first longitudinal axis and includes a first extension and a second extension. The first extension includes an outer surface, a projection extending from the outer surface and an inner surface defining a longitudinal cavity. The projection includes a ramp and a first locking element. The second arm includes a first extension and a second extension. The first extension of the second arm includes an outer surface and a projection extending therefrom. The projection of the second arm includes a ramp and a second locking element. The first extension of the second arm includes an inner surface defining a longitudinal cavity. The bone fastener includes a proximal portion that defines an implant cavity and a distal portion configured for penetrating tissue. The projections of the first and second arms are transversely moveable between a first configuration such that the projections extend beyond the outer surfaces of the first and second arms and a second configuration whereby the second extensions of the first and second arms axially translate within the respective longitudinal cavity and engage the respective ramp such that the projections are disposed in alignment with the outer surfaces and the locking elements engage the proximal portion of the bone fastener.

In one embodiment, the spinal implant system includes an extender and a bone fastener. The extender has a first arm and a second arm. The first arm defines a first longitudinal axis and includes a first extension and a second extension. The first extension includes an outer surface including a concave portion and a projection extending from the outer surface and pivotable relative thereto. The projection includes a tapered ramp extending between a proximal end having a first height and a distal end having a second, decreased height and a first locking element having a pointed arrowhead shaped tip and a flange extending transverse to the first longitudinal axis configured to engage a bone fastener. The first extension includes an inner surface defining a longitudinal cavity. The second extension includes a cavity extending between a first stop engageable with the tapered ramp to define a first moveable limit of the second extension and a second stop engageable with the tapered ramp to define a second moveable limit of the second extension along the first longitudinal axis. The cavity is configured for moveable disposal of the ramp. The first arm further includes an actuator having a locking element biased into engagement with the first extension and a depressible tab configured to disengage the locking element from the first extension. The actuator is fixed with a proximal end of the second extension and is configured to cause axial translation of the second extension within the longitudinal cavity. The second arm includes a first extension and a second extension. The first extension of the second arm includes an outer surface including a concave portion and a projection extending from the outer surface, which is pivotable, relative thereto. The projection of the second arm includes a tapered ramp extending between a proximal end having a first height and a distal end having a second, decreased height and a second locking element comprising a pointed arrowhead shaped tip and a flange extending transverse to the first longitudinal axis configured to engage a bone fastener. The first extension of the second arm includes an inner surface defining a longitudinal cavity. The second extension includes a cavity extending between a first stop engageable with the tapered ramp to define a first moveable limit of the second extension and a second stop engageable with the tapered ramp to define a second moveable limit of the second extension along the first longitudinal axis. The cavity is configured for moveable disposal of the ramp. The second arm further includes an actuator having a locking element biased into engagement with the first extension and a depressible tab configured to disengage the locking element from the first extension. The actuator is fixed with a proximal end of the second extension and is configured to cause axial translation of the second extension within the longitudinal cavity. The distal ends of the first extensions of the first and second arms each include a first flange and a second flange configured for capture of the bone fastener. The bone fastener includes a proximal portion having a pair of spaced apart arms that define an implant cavity and a distal portion configured for penetrating tissue. Each of the spaced apart arms include an outer surface and first and second side surfaces each having a longitudinal groove extending parallel to the first longitudinal axis configured to engage the first flange or the second flange of the first extensions. The outer surface of the spaced apart arms includes a longitudinal channel extending parallel to the first longitudinal axis configured for disposal of the pointed arrowhead shaped tip. The concave portions of the first extensions define an implant cavity. The projections of the first and second arms are transversely moveable between a first configuration such that the projections extend beyond the outer surfaces and a second configuration whereby the second extensions axially translate within the respective longitudinal cavity and engage the respective ramp such that the projections are disposed in alignment with the outer surfaces and the locking elements engage the proximal portion of the bone fastener.

BRIEF DESCRIPTION OF THE DRAWINGS

The present disclosure will become more readily apparent from the specific description accompanied by the following drawings, in which:

FIG. 17 is a break away, cross section view of the system shown in FIG. 1;

FIG. 18 is a break away, cross section view of the system shown in FIG. 1; and

Like reference numerals indicate similar parts throughout the figures.

DETAILED DESCRIPTION

Figure 1:
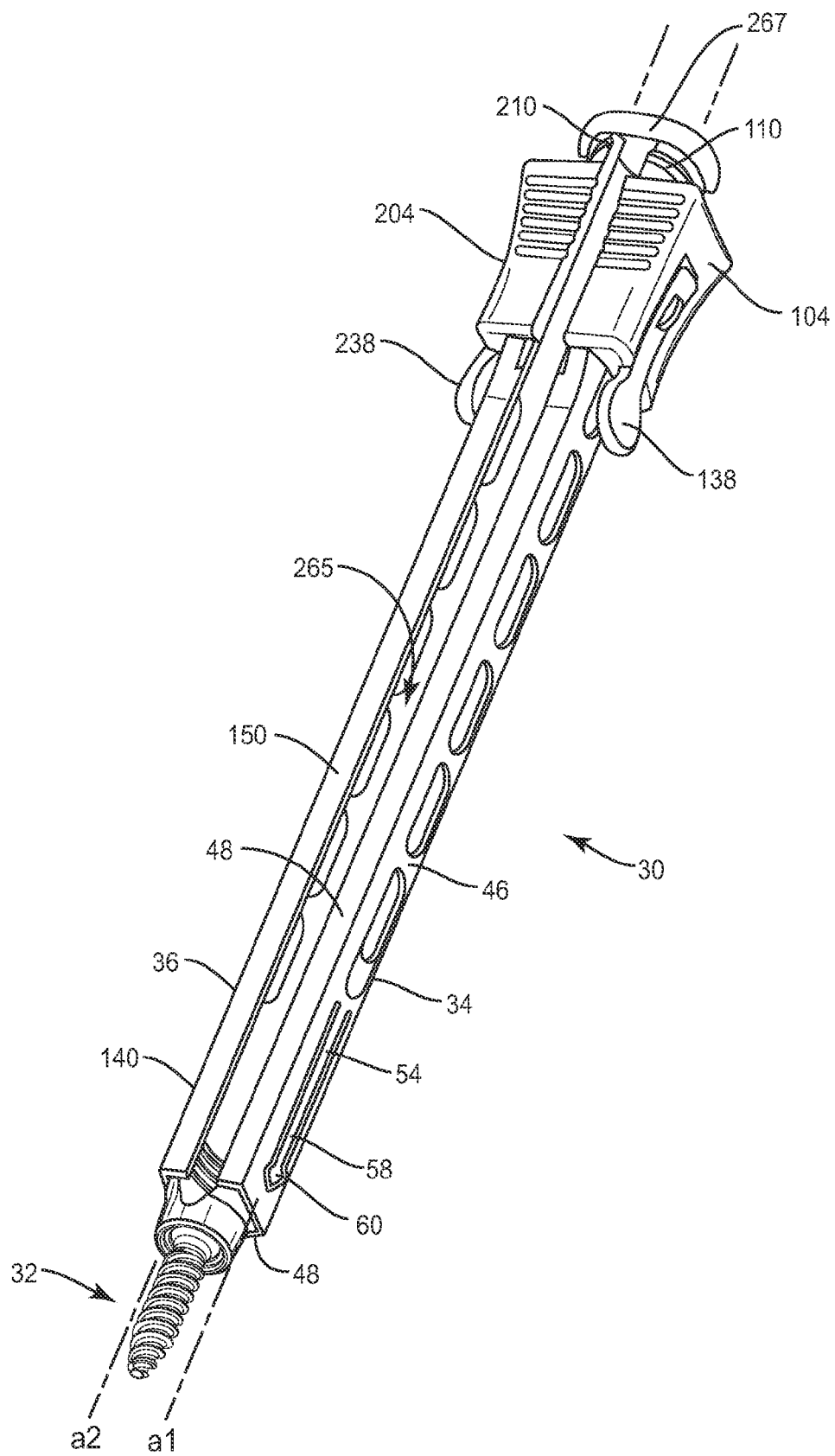
FIG. 1 is a perspective view of one particular embodiment of the system in accordance with the principles of the present disclosure.
Figure 2:
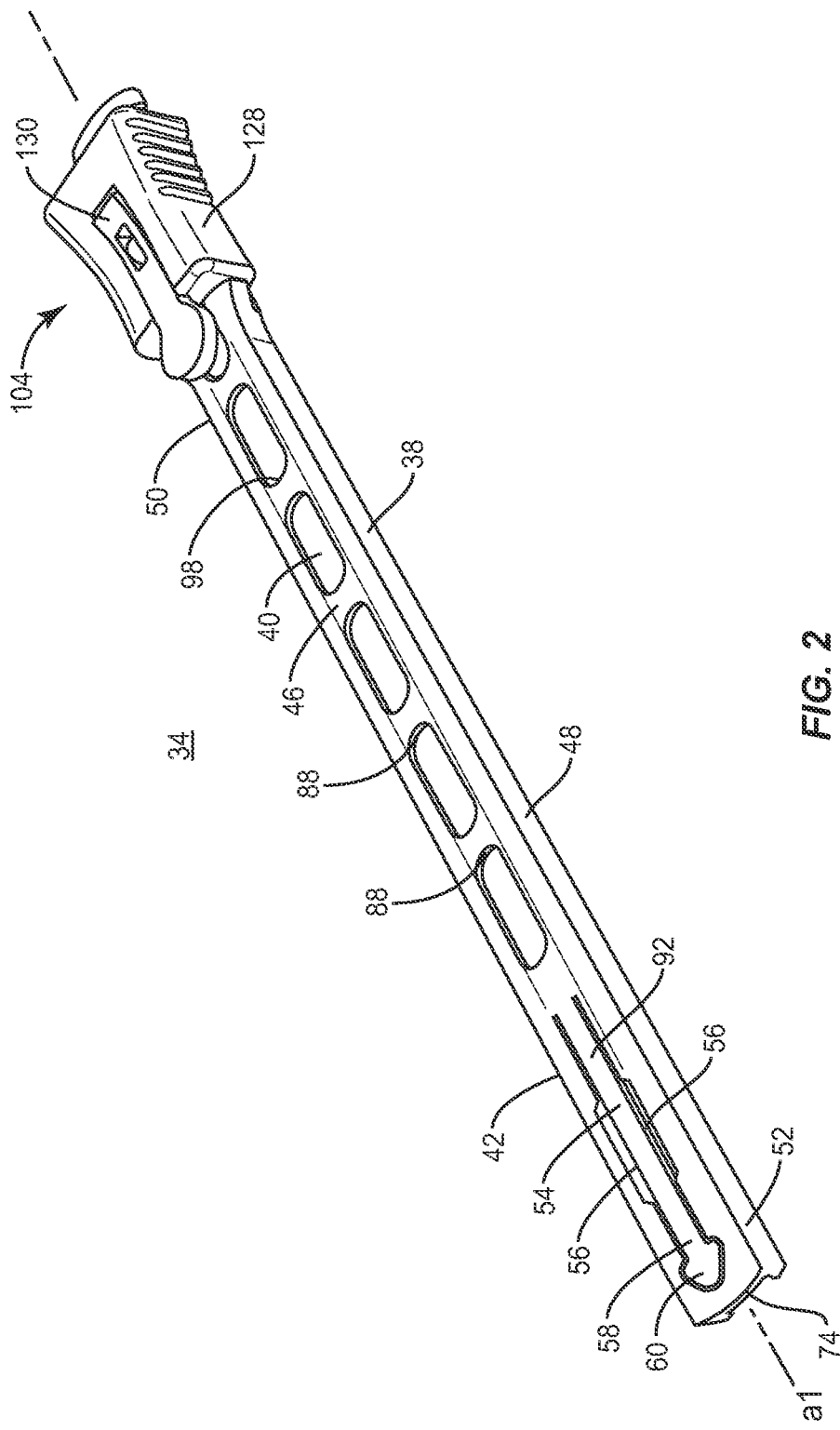
FIG. 2 is a perspective view of a component of the system shown in FIG. 1.
Figure 3:
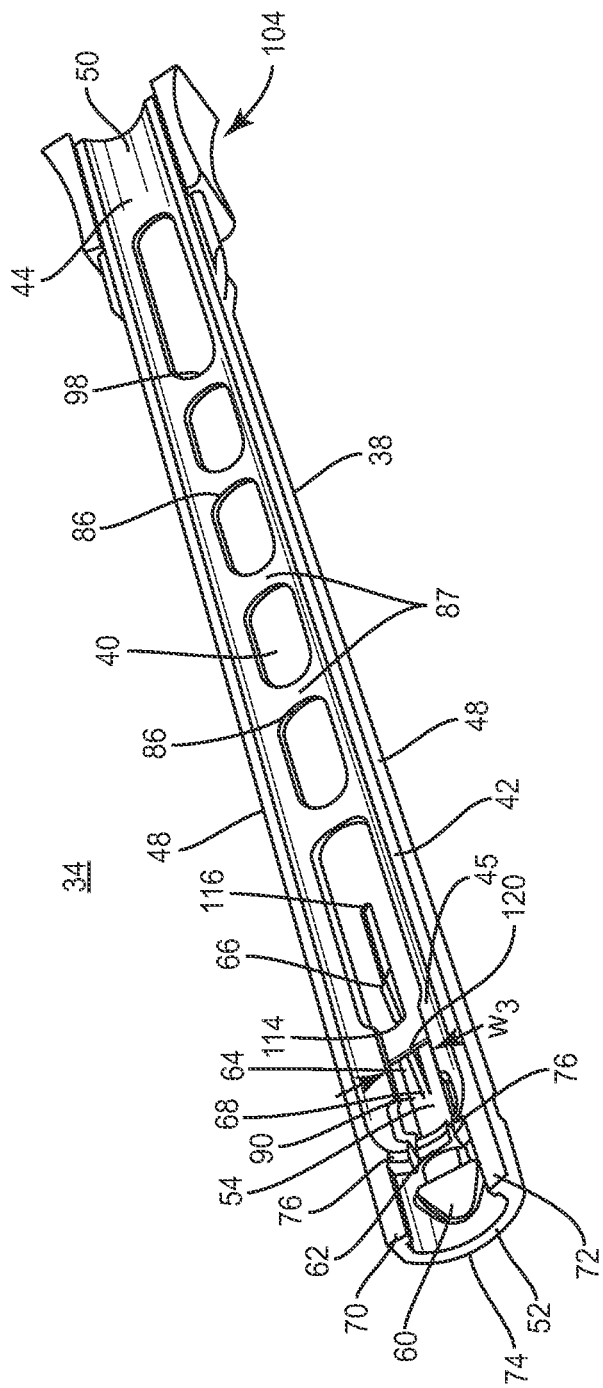
FIG. 3 is a perspective view of the component shown in FIG. 2.
Figure 4:
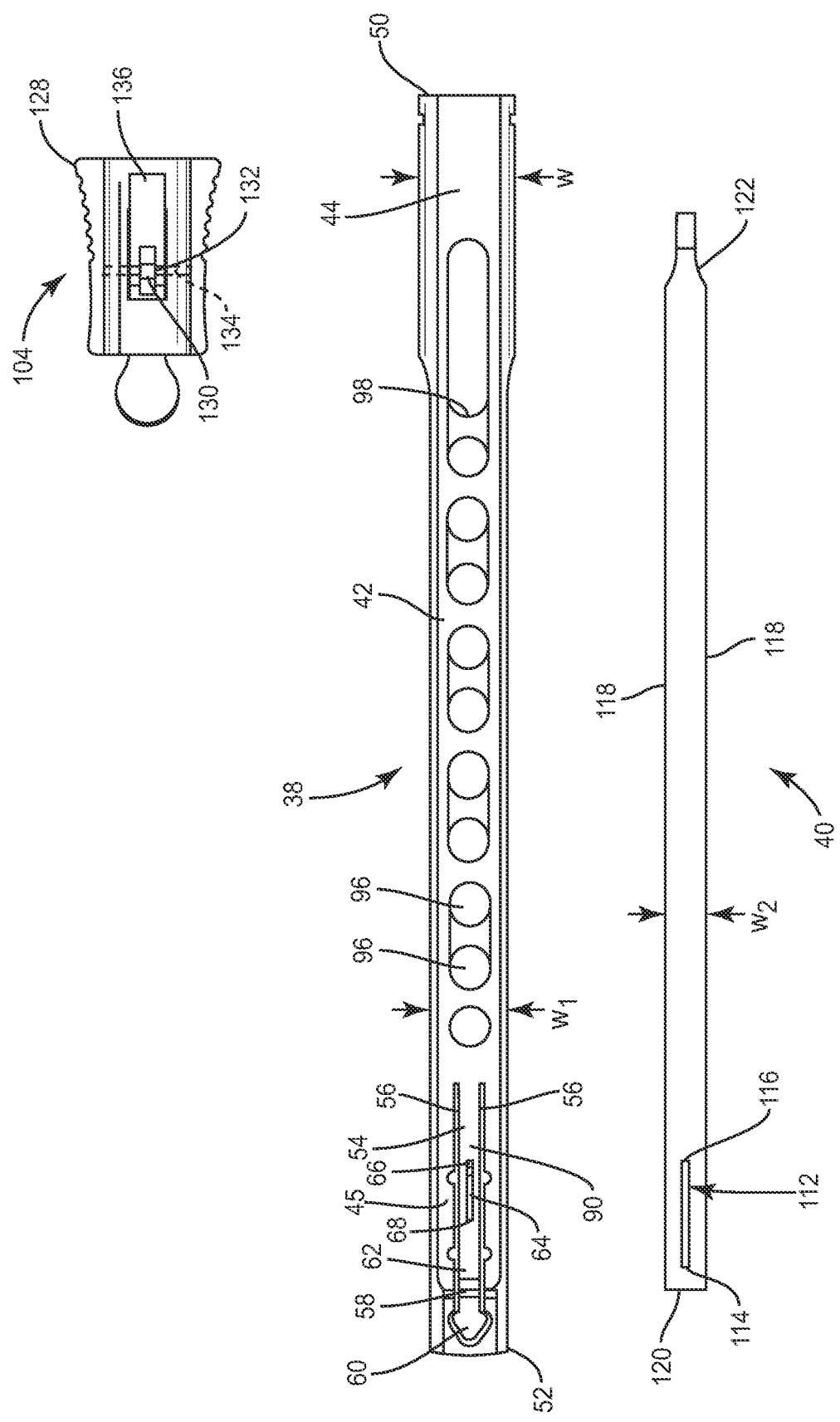
FIG. 4 is a side view of the component shown in FIG. 2, with parts separated.
Figure 5:
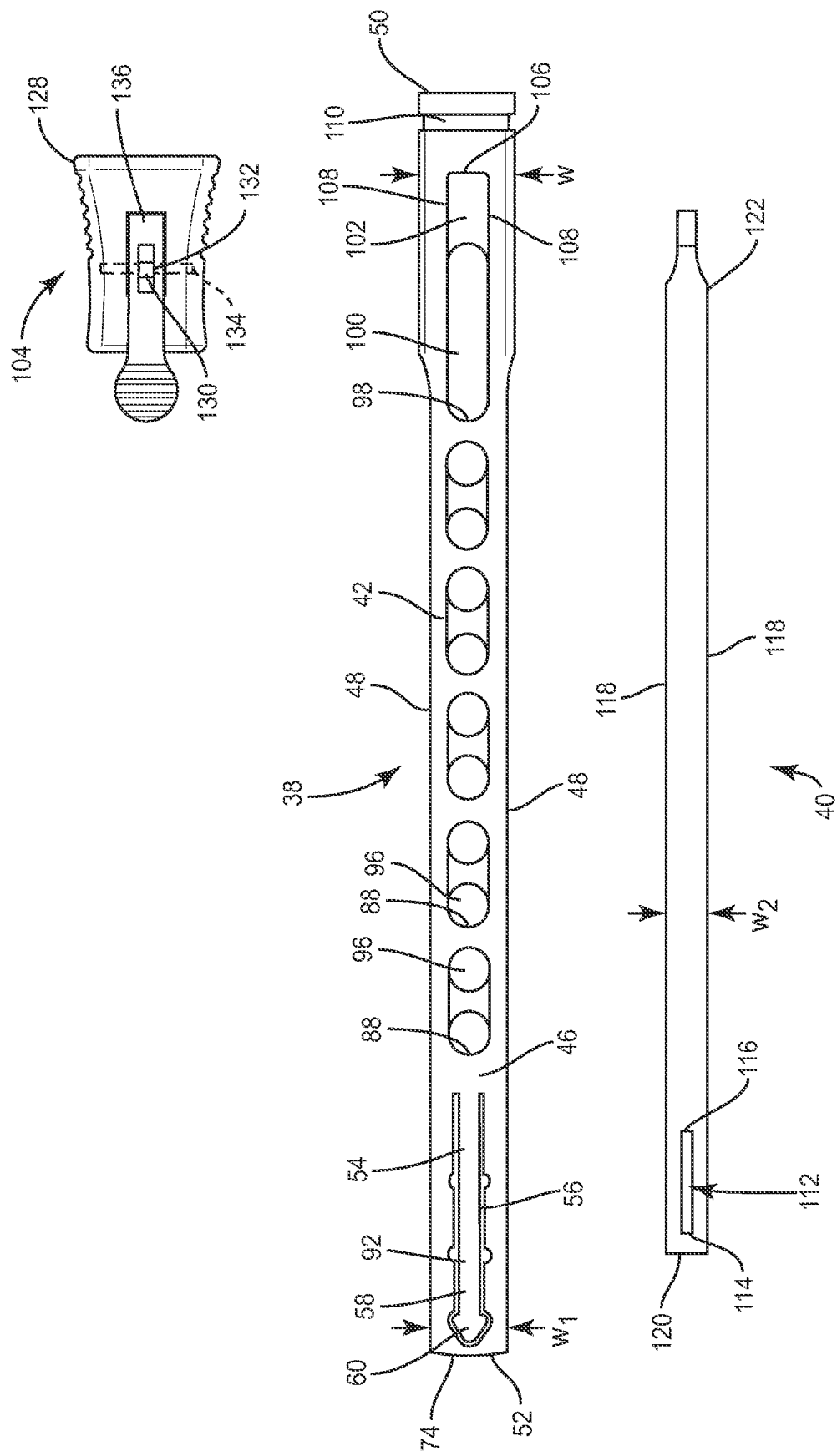
FIG. 5 is a perspective view of the component shown in FIG. 2, with parts separated.
Figure 6:
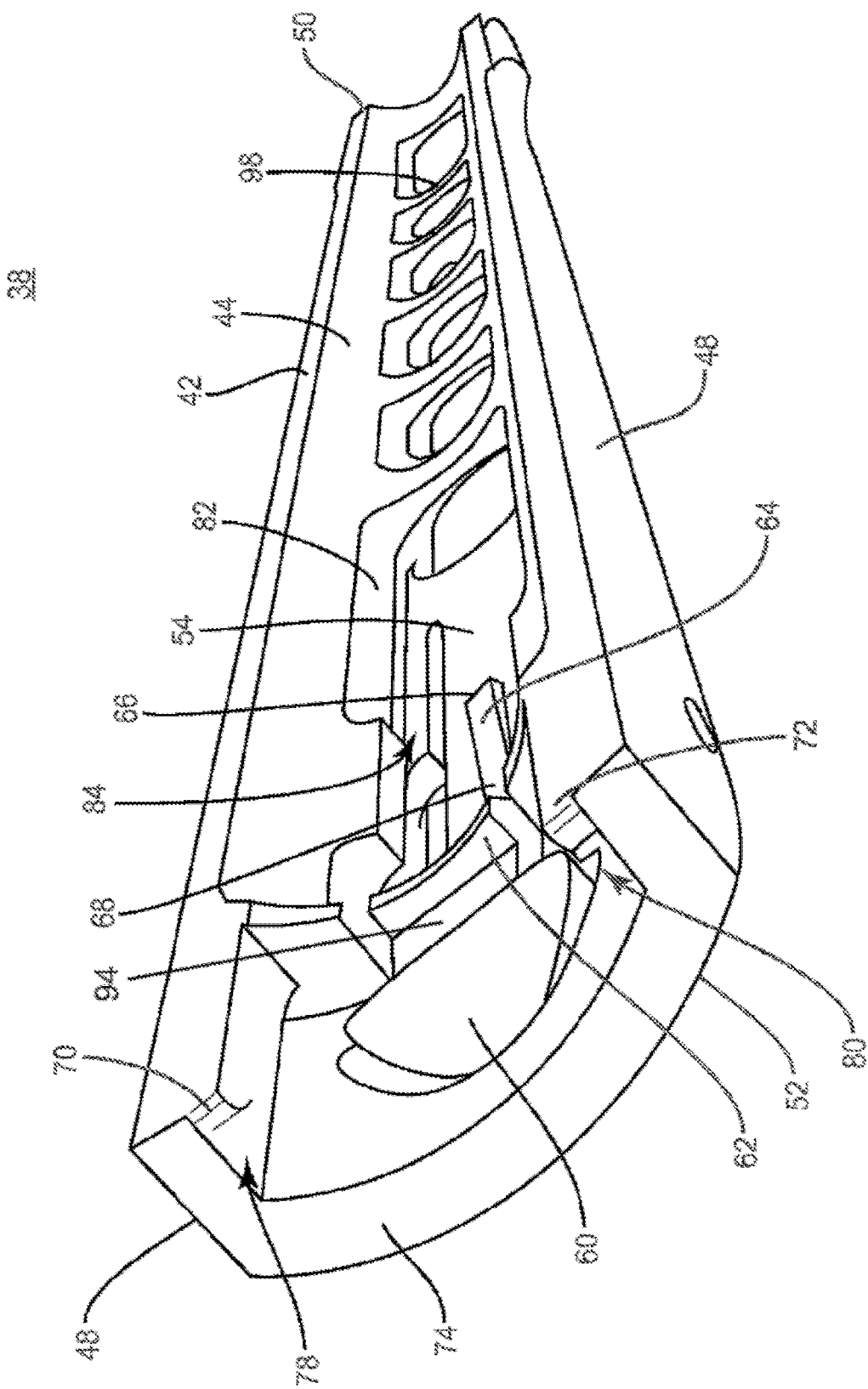
FIG. 6 is a perspective view of the component shown in FIG. 2.
Figure 7:
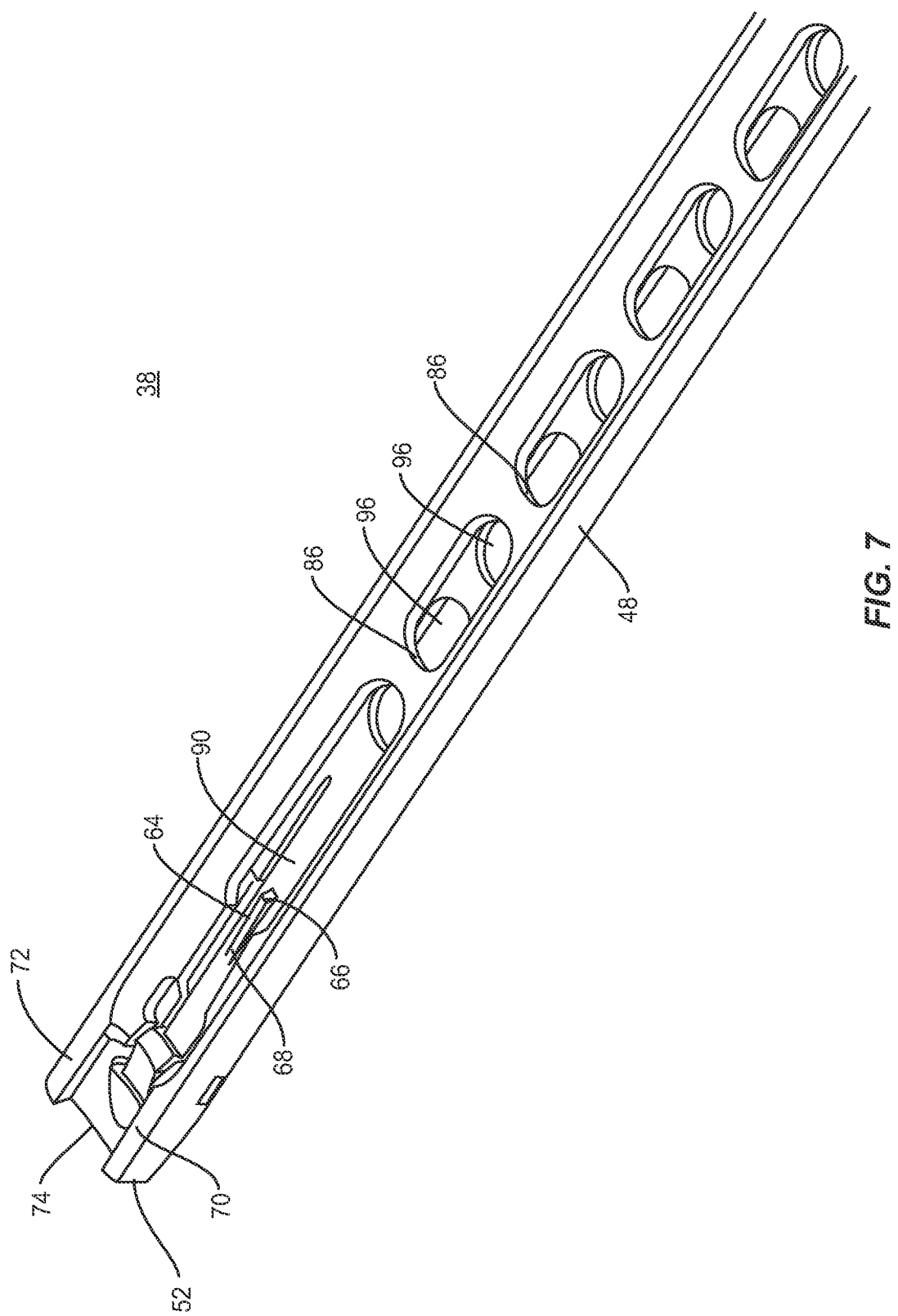
FIG. 7 is a break away, perspective view of the component shown in FIG. 6.
Figure 8:
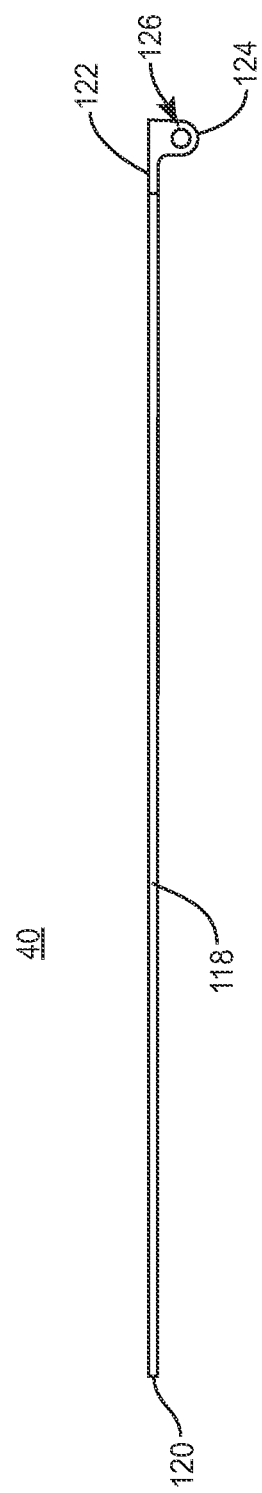
FIG. 8 is a side view of a component of the system shown in FIG. 1.
Figure 9:
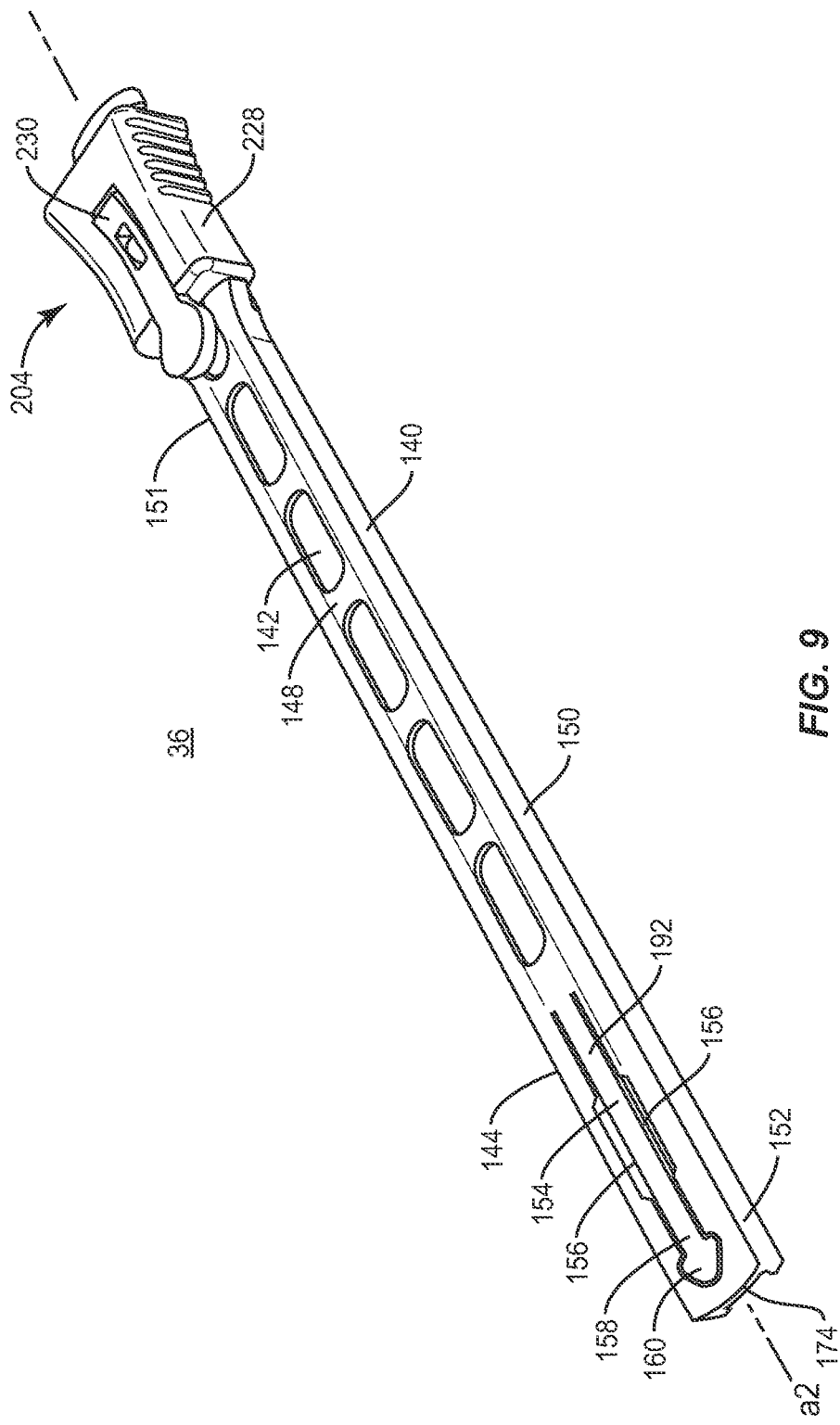
FIG. 9 is a perspective view of a component of the system shown in FIG. 1.
Figure 10:
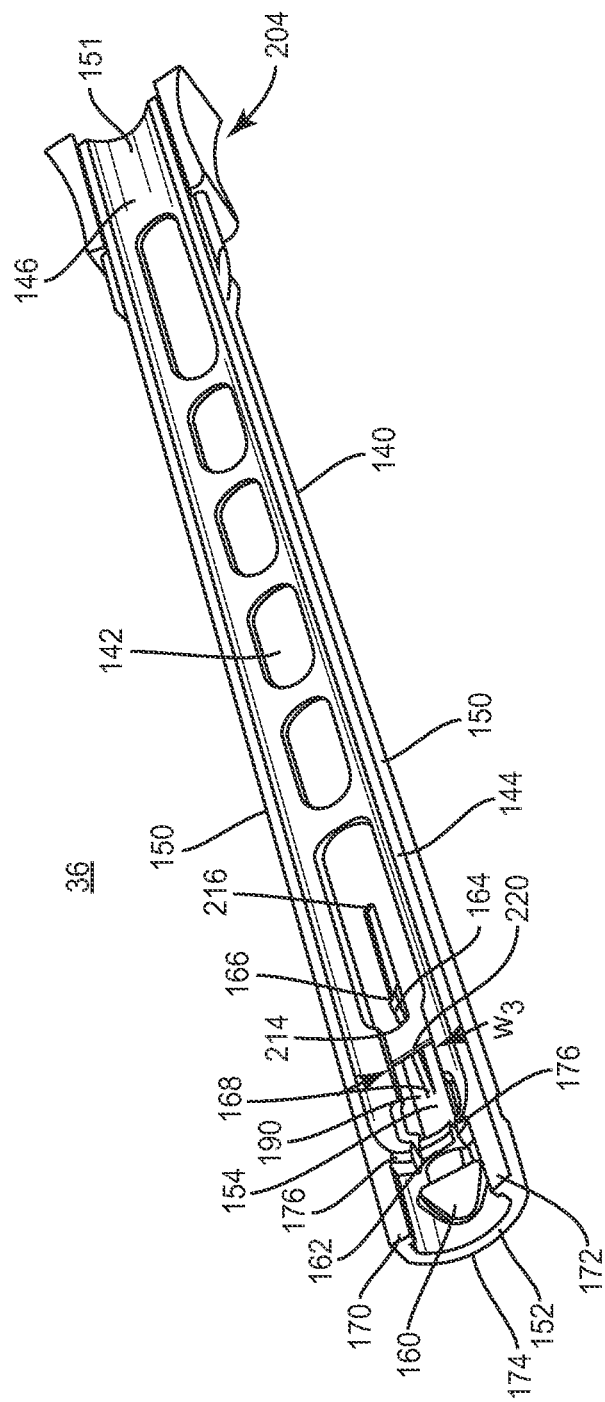
FIG. 10 is a perspective view of the component shown in FIG. 9.
Figure 11:
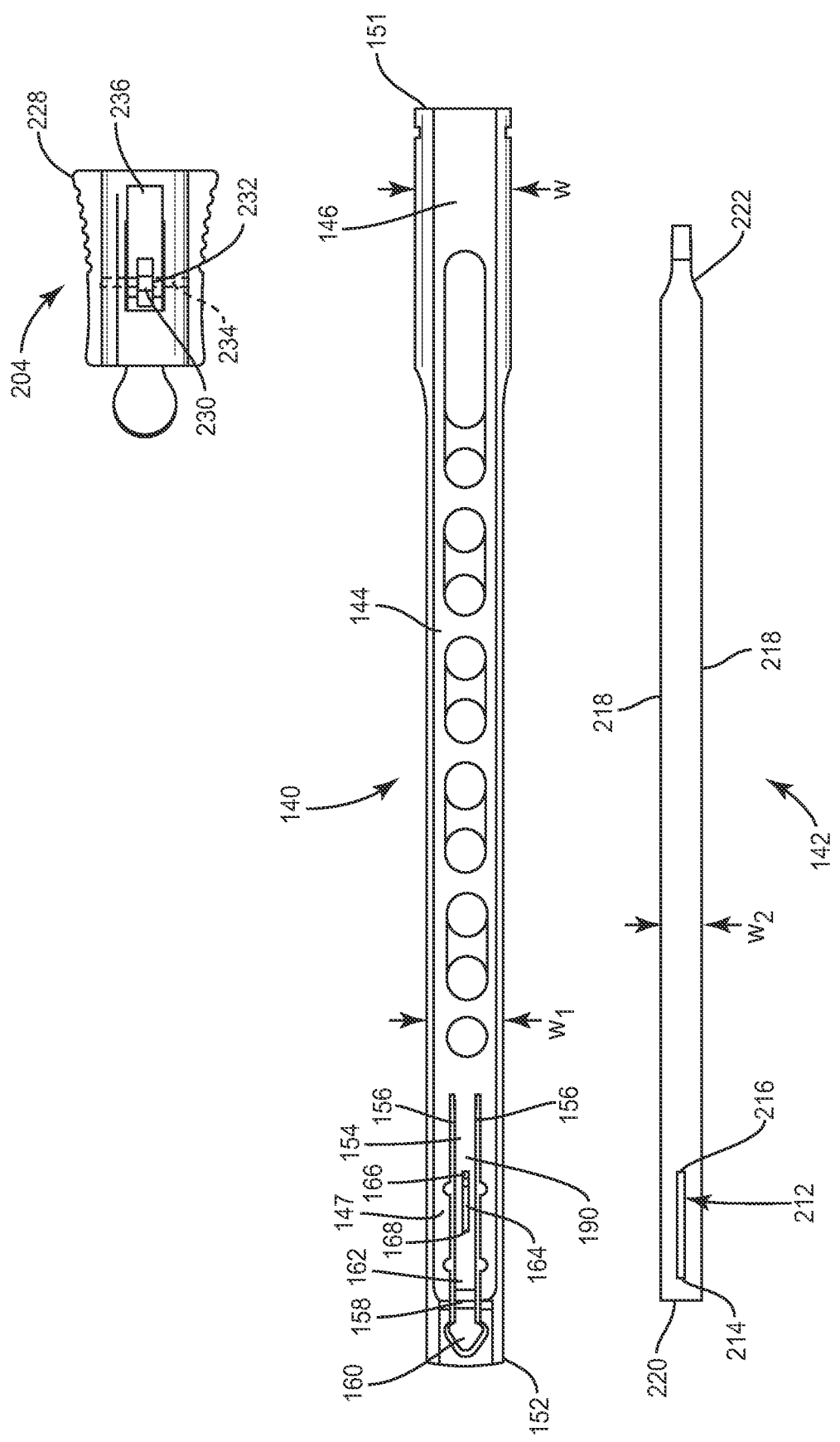
FIG. 11 is a side view of the component shown in FIG. 9, with parts separated.
Figure 12:
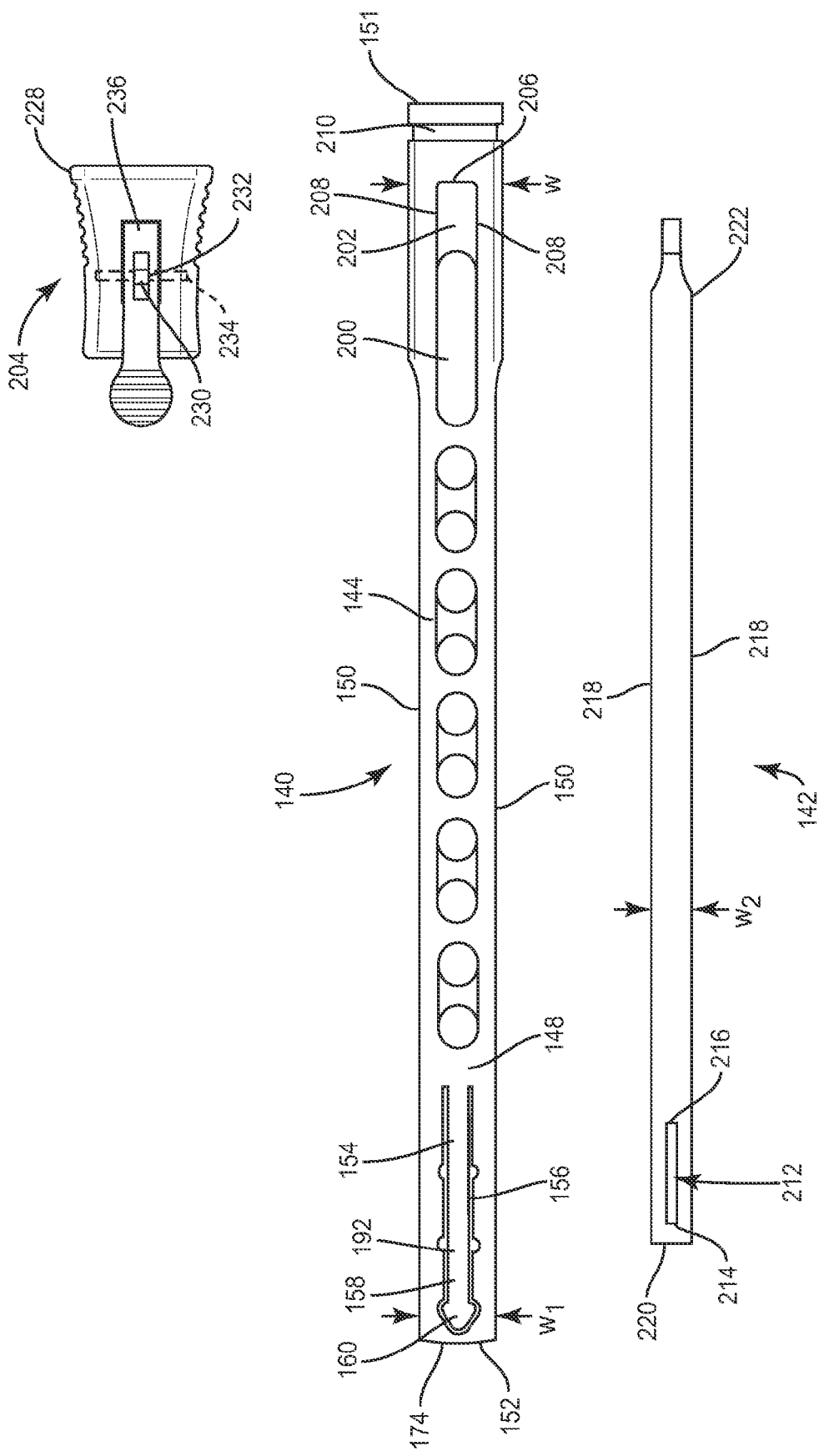
FIG. 12 is a perspective view of the component shown in FIG. 9, with parts separated.
Figure 13:
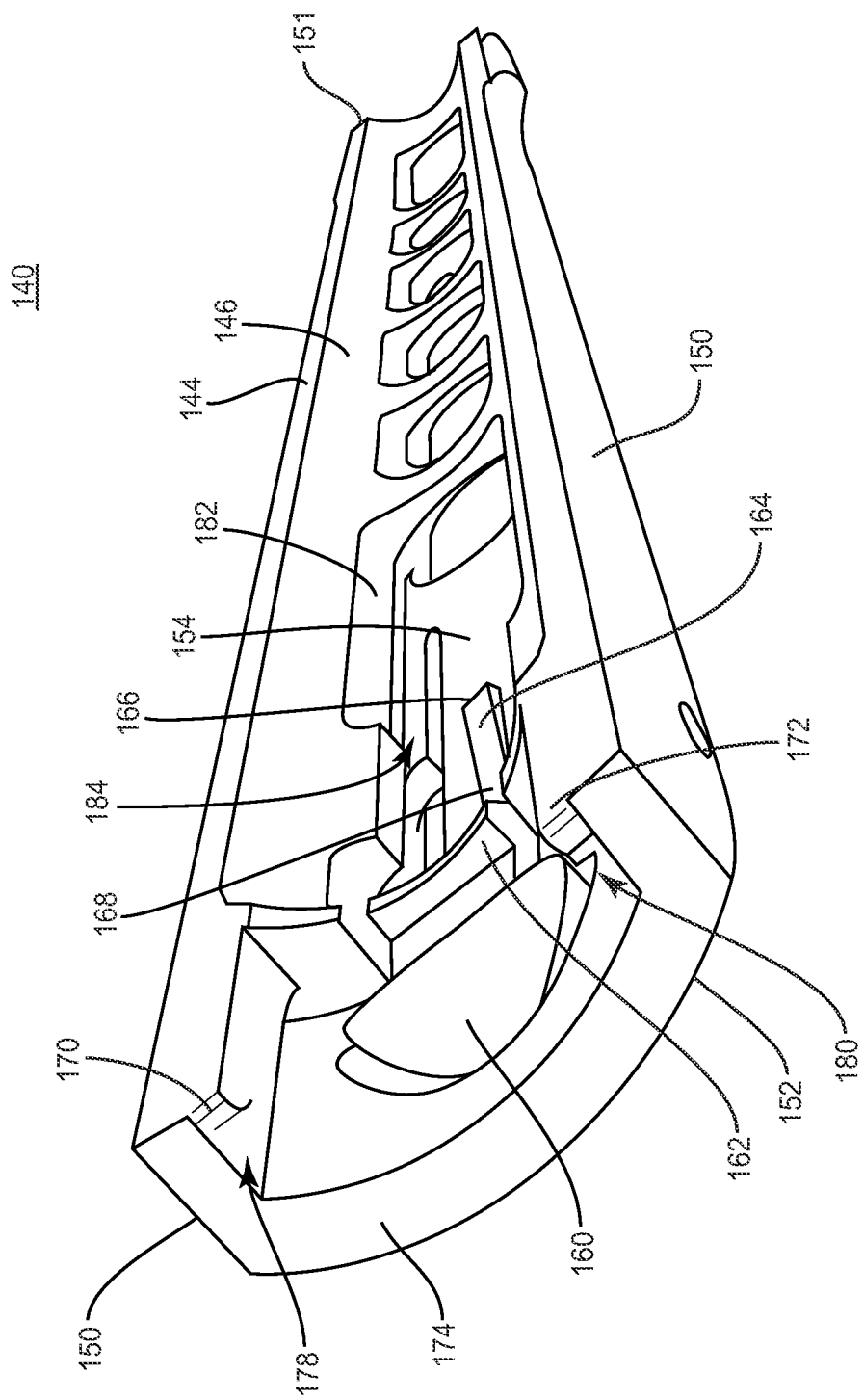
FIG. 13 is a perspective view of the component shown in FIG. 9.
Figure 14:
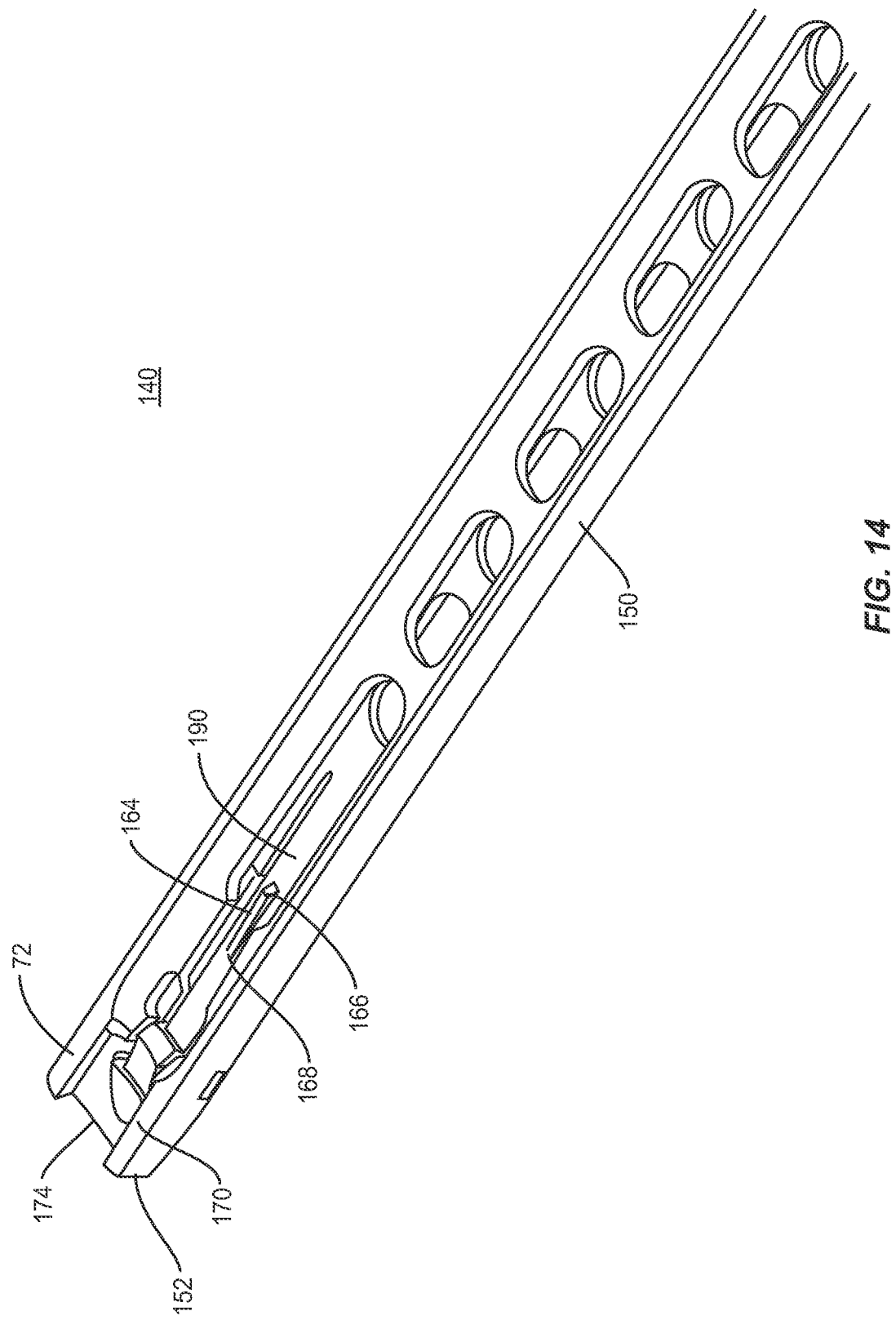
FIG. 14 is a break away, perspective view of the component shown in FIG. 13.
Figure 15:
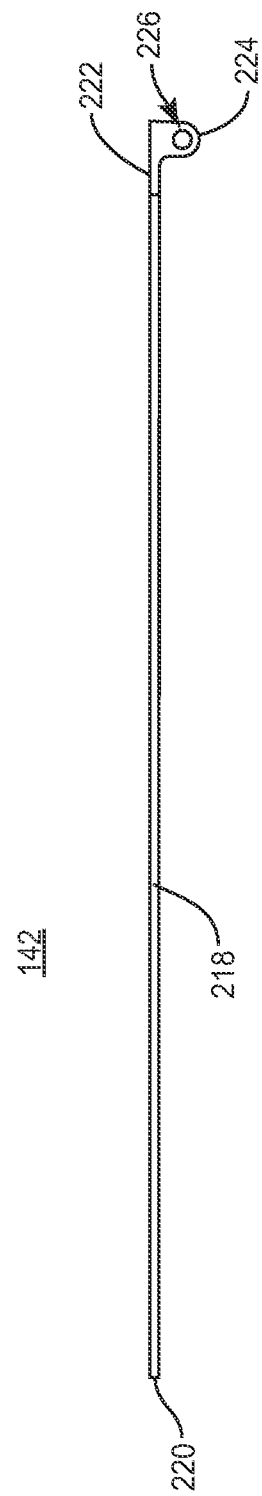
FIG. 15 is a side view of a component of the system shown in FIG. 1.
Figure 16:
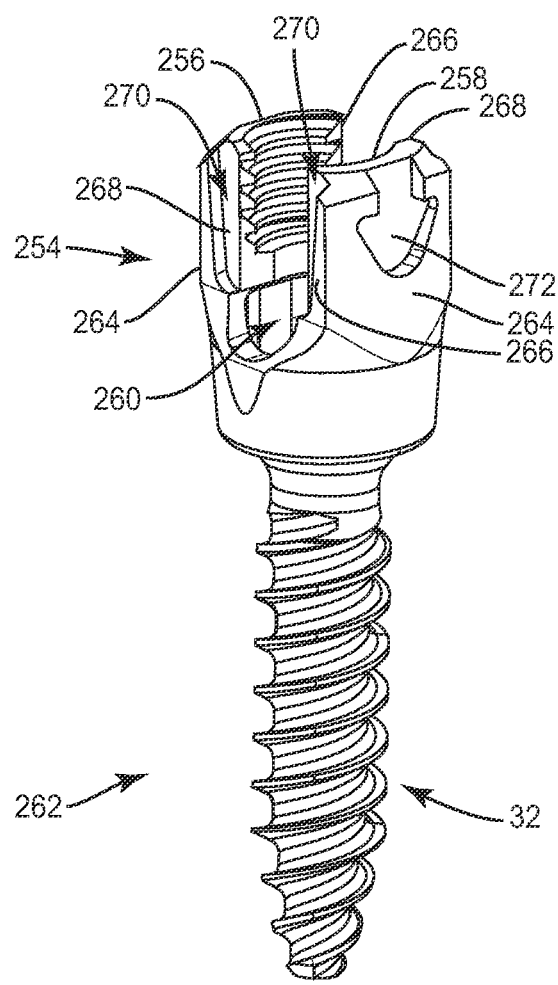
FIG. 16 is a perspective view of a component of the system shown in FIG. 1.

The exemplary embodiments of the spinal implant system and related methods of use disclosed are discussed in terms of medical devices for the treatment of musculoskeletal disorders and more particularly, in terms of a surgical system for implant delivery to a surgical site. It is envisioned that the spinal implant system may be utilized percutaneously at multiple levels relative to a plane, such as, for example, a plane of a body of a patient. It is contemplated that the spinal implant system can include multiple bone fasteners, each fixed at a different level relative to a plane, such as, for example, a plane of a body of a patient, such that each bone fastener engages a connective element, such as, for example, a vertebral rod. It is further contemplated that the connective element may include a targeting device to allow for placement of the bone fasteners.

It is envisioned that the system may include instruments that are connected or attached to an extender(s) such as, for example, a lateral translation handle or derotaton instruments. It is further envisioned that the system may have an extender with a quick release mechanism to allow the extender to slide into engagement with a bone fastener. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The present embodiments may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-18, there is illustrated components of a surgical system, such as, for example, a spinal implant system in accordance with the principles of the present disclosure.

The components of the spinal implant system can be fabricated from biologically acceptable materials suitable for medical applications, including metals, synthetic polymers, ceramics and bone material and/or their composites, depending on the particular application and/or preference of a medical practitioner. For example, the components of the spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the spinal implant system, individually or collectively, may also be fabricated from a heterogeneous material such as a combination of two or more of the above-described materials. The components of the spinal implant system may be monolithically formed, integrally connected or include fastening elements and/or instruments, as described herein.

The spinal implant system is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that the spinal implant system and method may be employed with treatments using minimally invasive and percutaneous techniques.

The spinal implant system includes an extender 30 and a bone fastener 32. Extender 30 includes a first arm 34 and a second arm 36. First arm 34 defines a first longitudinal axis a1 and includes a first extension 38 and a second extension 40. First extension 38 has an outer surface 42 including a concave portion 44 and a convex portion 46 opposite concave portion 44. First extension 38 includes planar side surfaces 48 extending between concave and convex portions 42, 44. Concave portion 44 includes an extension retaining portion 45 configured to retain at least a portion of second extension 40 within a longitudinal cavity 84. First extension 38 extends between a proximal end 50 having a width w and a distal end 52 having a reduced with w1. It is envisioned that all or only a portion of concave portion 44, convex portion 46 and/or side surfaces 48 may be variously configured and dimensioned, such as, for example, planar, concave, convex, polygonal, irregular, uniform, non-uniform, staggered, tapered, consistent or variable, depending on the requirements of a particular application.

First arm 34 includes a projection 54 extending from outer surface 42 and pivotable relative thereto. Projection 54 includes a first surface 90 and a second surface 92, opposite first surface 90. Projection 54 includes planar side surfaces 56 and a first locking element 58 at a distal end of projection 54 extending between side surfaces 56. First locking element 58 has a tip 60, such as, for example, a pointed arrowhead shaped tip. Tip 60 is continuous with second surface 92 of projection 54 and extends perpendicularly from first surface 90. A portion of tip 60, which extends perpendicularly from first surface 90 of projection 54 includes a flange 62 extending perpendicularly from tip 60 and transverse to first longitudinal axis a1 configured to engage bone fastener 32. Flange 62 is convexly curved between a first end and a second end. Tip 60 is configured for disposal in bone fastener 32 to engage first arm 34 with bone fastener 32 such that flange 62 engages at least a portion of bone fastener 32 to prevent movement of bone fastener 32 relative to first arm 34 in one direction. A portion of tip 60, which extends perpendicularly from first surface 90 of projection 54 includes an undercut 94 extending transverse to first longitudinal axis a1 through tip 60. Undercut 94 defines a substantially rectangular channel configured for disposal of at least a portion of second extension 40 to prevent second extension 40 from moving relative to first extension 38 in one direction. It is contemplated that all or only a portion of tip 60, flange 62 and/or undercut 94 may be variously configured and dimensioned, such as, for example, round, oval, oblong, square, rectangular, polygonal, irregular, uniform, non-uniform, offset, staggered, tapered, consistent or variable, depending on the requirements of a particular application.

First surface 90 of projection 54 includes a tapered ramp 64 extending from outer surface 42 between a proximal end 66 having a first height and a distal end 68 having a second, decreased height. It is envisioned that projection 54 may extend from outer surface 42 such that proximal end 66 of ramp 64 is disposed at an angle relative to outer surface 42, depending on the requirements of a particular application. Ramp 64 is substantially planar between proximal and distal ends 66, 68. Ramp 64 has a width that is less than a width of projection 54 between side surfaces 56 of projection 54 such that ramp is disposed inward a distance from each side surface 56. It is envisioned that ramp 64 may be disposed in the center of projection 54 such that ramp 64 is equidistant from each side surface 56. It is further envisioned that ramp 64 may be offset such that ramp 64 is disposed closer to one side surface 56 than an opposite side surface 56. It is contemplated that all or only a portion of ramp 64 may be variously configured and dimensioned, such as, for example, planar, concave, convex, polygonal, irregular, uniform, non-uniform, staggered, tapered, consistent or variable, depending on the requirements of a particular application.

Side surfaces 48 of first extension 38 include a first flange 70 and a second flange 72 each extending transverse to first longitudinal axis a1 between a distal face 74 of first extension 38 and a concavely curved transverse wall 76 along first longitudinal axis a1. Transverse wall 76 is coaxial with flange 62 and has a curvature that is continuous with that of flange 62 such that transverse wall 76 and flange 62 define a U-shaped wall. Transverse wall 76, like flange 62, engages at least a portion of bone fastener 32 to prevent movement of bone fastener 32 relative to first arm 34 in one direction. First flange 70 defines a first groove 78 extending between outer surface 42 and first flange 70 and second flange 72 defines a second groove 80 extending between outer surface 42 and second flange 72. First and second grooves 78, 80 are each configured for disposal of at least a portion of bone fastener 32 to engage first arm 34 with bone fastener 32 and prevent rotation of first arm 34 relative to bone fastener 32 about first longitudinal axis a1. It is contemplated that first flange 70 and/or second flange 72 may be disposed at alternate orientations relative to side surfaces 48, such as, for example, transverse, perpendicular, parallel and/or other angular orientations such as acute or obtuse, co-axial and/or may be offset or staggered. It is envisioned that all or only a portion of flange 62 and/or transverse wall 76 may be variously configured and dimensioned, such as, for example, planar, concave, convex, polygonal, irregular, uniform, non-uniform, staggered, tapered, consistent or variable, depending on the requirements of a particular application.

First extension 38 includes an inner surface 82 defining longitudinal cavity 84 configured for axial translation of second extension 40 therein. First extension 38 includes at least one oblong opening 86 extending through concave portion 44 and at least one oblong opening 88 extending through convex portion 46 and offset from oblong opening(s) 86. First extension 38 includes four (4) oblong openings 86 and four (4) oblong openings 88, each being equally spaced apart from one another. It is envisioned that first extension 38 may include one or a plurality of oblong openings 86, 88. Oblong openings 86, 88 overlap one another to define at least one circular opening 96 extending through concave portion 44 and convex portion 46. First extension 38 includes ten (10) circular openings 96. It is envisioned that first extension 38 may include one or a plurality of circular openings 96. It is further envisioned that all or only a portion of oblong opening (s) 86, oblong opening(s) 88 and/or circular opening(s) 96 may be variously configured and dimensioned, such as, for example, round, oval, oblong, square, rectangular, polygonal, irregular, uniform, non-uniform, offset, staggered, tapered, consistent or variable, depending on the requirements of a particular application.

Concave portion 44 includes at least one rail 87 extending between side surfaces 48 and oblong openings 86 configured to retain at least a portion of second extension 40 within longitudinal cavity 84. Concave portion 44 includes five (5) rails 87, each being equally spaced apart from one another. It is envisioned that first extension 38 may include one or a plurality of rails 87. Rails 87 include concavely curved side surfaces. It is envisioned that all or only a portion of rails 87 may be variously configured and dimensioned, such as, for example, planar, concave, convex, polygonal, irregular, uniform, non-uniform, staggered, tapered, consistent or variable, depending on the requirements of a particular application.

Proximal end 50 of first extension 38 includes a proximal opening 98 having an oblong shaped first portion 100 extending through concave portion 44 and convex portion 46 of first extension 38. Proximal opening 98 includes a second portion 102, which extends through convex portion 46, but does not extend through concave portion 44. Second portion 102 defines a crevice configured for engagement with at least a portion of an actuator 104 to prevent axial translation of second extension 40 within longitudinal cavity 84. Second portion 102 includes a planar end wall 106 extending between planar sidewalls 108. It is envisioned that all or only a portion of proximal opening 98, including all or only a portion of first and second portions 100, 102 may be variously configured and dimensioned, such as, for example, round, oval, oblong, square, rectangular, polygonal, irregular, uniform, non-uniform, offset, staggered, tapered, consistent or variable, depending on the requirements of a particular application. It is further envisioned that all or only a portion of second portion 102 may be variously configured and dimensioned, such as, for example, planar, concave, convex, polygonal, irregular, uniform, non-uniform, staggered, tapered, consistent or variable, depending on the requirements of a particular application.

Proximal end 50 of first extension 38 includes a transverse groove 110 extending transverse to first longitudinal axis a1 through convex portion 46 configured to allow for the attachment of other instruments, such as, for example, drivers and rod reduction instruments. This feature allows extender 30 to become part of an instrument system used in spinal and other surgical procedures. It is envisioned that transverse groove 110 may have alternate surface configurations to enhance fixation with an instrument such as, for example, rough, arcuate, undulating, mesh, porous, semi-porous, dimpled and/or textured according to the requirements of a particular application.

Second extension 40 is configured for axial translation within longitudinal cavity 84 and includes a cavity 112 configured for moveable disposal of ramp 64 extending between a first stop 114 engageable with ramp 64 to define a first moveable limit of second extension 40 and a second stop 116 engageable with ramp 64 to define a second moveable limit of second extension 40 along first longitudinal axis a1. First and second stops 114, 116 are planar and extend between planar side surfaces. Second extension 40 is substantially rectangular and includes planar sidewalls 118 extending between a planar distal face 120 and a proximal end 122 having a curved protrusion 124 extending perpendicularly from second extension 40 including an eyelet 126 extending transverse to first longitudinal axis a1 through protrusion 124. Second extension 40 has a width w2, which is less than a width of longitudinal cavity 84 such that second extension 40 can translate axially within longitudinal cavity 84. Width w2 of second extension 40 is greater than a width w3 of extension retaining portion 45 such that extension retaining portion 45 and rails 87 retain second extension 40 within longitudinal cavity 84. It is envisioned that all or only a portion of second extension 40 may be variously configured and dimensioned, such as, for example, round, oval, oblong, square, rectangular, polygonal, irregular, uniform, non-uniform, offset, staggered, tapered, consistent or variable, depending on the requirements of a particular application. It is further envisioned that all or only a portion of cavity 112 may be variously configured and dimensioned, such as, for example, planar, concave, convex, polygonal, irregular, uniform, non-uniform, staggered, tapered, consistent or variable, depending on the requirements of a particular application.

Second extension 40 may be advanced proximally within longitudinal cavity 84 such that a distal end of second extension 40 moves from distal end 68 of ramp 64 to proximal end 66 of ramp 64. Second surface 92 of projection 54 extends beyond outer surface 42 of first extension 38 as the distal end of second extension 40 is advanced proximally over ramp 64. Second extension 40 may be moved proximally within longitudinal cavity 84 until proximal end 66 of ramp 64 engages first stop 114 to prevent second extension 40 from further advancing proximally within longitudinal cavity 84. When ramp 64 engages first stop 114, first arm 34 is in a first configuration such that second surface 92 of projection 54 extends beyond outer surface 42 of first extension 38.

Second extension 40 may be advanced distally within longitudinal cavity 84 such that the distal end of second extension 40 moves from proximal end 68 to distal end 68 of ramp 64, to move first arm 34 from the first configuration to a second configuration. Second surface 92 moves inwardly as the distal end of second extension 40 is advanced distally over ramp 64 such that ramp 64 recesses and/or is disposed within cavity 112. Second surface 92 is disposed in alignment with outer surface 42 of first extension 38. Second extension 40 is advanced distally within longitudinal cavity 84 until distal end 68 engages second stop 116 and distal face 120 of second extension 40 is disposed within undercut 94 to prevent second extension 40 from further advancing distally within longitudinal cavity 84. Ramp 64 engages second stop 116 and first arm 34 is disposed in the second configuration such that second surface 92 is aligned with outer surface 42.

Actuator 104 includes a body portion 128 configured to moveably engage at least a portion of proximal end 50. Actuator 104 includes a locking element 130 having a circular opening 132 extending transverse to first longitudinal axis a1 through locking element 130. A cylindrical pin 134 is inserted through eyelet 126 in second extension 40 and opening 132 in locking element 130 when second extension 40 is retained within longitudinal cavity 84 such that locking element 130 is pivotable relative to first and second extensions 38, 40. Axial translation of actuator 104 causes axial translation of second extension 40 within longitudinal cavity 84. Locking element 130 includes a first end 136 having a planar face extending between planar sidewalls and is configured for disposal within second portion 102 of first extension 38 to prevent axial translation of second extension 40 within longitudinal cavity 84. Locking element 130 is biased into engagement with second portion 102 of first extension 38 via a spring (not shown) positioned between first end 136 of locking member 130 and body portion 128. A depressible tab 138 is positioned at a second end of locking element 136, opposite first end 136. Depressible tab 138 is pivotable about pin 134 such that advancing depressible tab 138 in one direction moves first end 136 of activator 104 in an opposite direction such that first end is removed from second portion 102 of first extension 38, which disengages locking element 130 from first extension 38.

Second arm 36 defines a second longitudinal axis a2 and includes a first extension 140 and a second extension 142, similar to arm 34 described above. First extension 140 has an outer surface 144 including a concave portion 146 and a convex portion 148 opposite concave portion 146. First extension 140 includes planar side surfaces 150 extending between concave and convex portions 146, 148. Concave portion 146 includes an extension retaining portion 147 configured to retain at least a portion of second extension 142 within a longitudinal cavity 184. First extension 140 extends between a proximal end 151 and a distal end 152.

Second arm 36 includes a projection 154 extending from outer surface 144 and pivotable relative thereto. Projection 154 includes a first surface 190 and a second surface 192, opposite first surface 190. Projection 154 includes planar side surfaces 156 and a first locking element 158 at a distal end of projection 154 extending between side surfaces 156. First locking element 158 has a pointed arrowhead shaped tip 160. A portion of tip 160 extends perpendicularly from first surface 190 and includes a flange 162 extending perpendicularly from tip 160 and transverse to second longitudinal axis a2. A portion of tip 160 includes an undercut 194 extending transverse to second longitudinal axis a2. Undercut 194 defines a substantially rectangular channel configured for disposal of at least a portion of second extension 142 to prevent second extension 142 from moving relative to first extension 140 in one direction.

First surface 190 of projection 154 includes a tapered ramp 164 extending from outer surface 142 between a proximal end 166 having a first height and a distal end 168 having a second, decreased height. Ramp 164 is substantially planar between proximal and distal ends 166, 168. Ramp 164 has a width that is less than a width of projection 154 between side surfaces 156 of projection 154 such that ramp is disposed inward a distance from each side surface 156.

Side surfaces 150 of first extension 140 include a first flange 170 and a second flange 172 each extending transverse to second longitudinal axis a2 between a distal face 174 and a concavely curved transverse wall 176 along second longitudinal axis a2. Transverse wall 176 is coaxial with flange 162 and has a curvature that is continuous with that of flange 162 such that transverse wall 176 and flange 162 define a U-shaped wall. Transverse wall 176 engages at least a portion of bone fastener 32 to prevent movement of bone fastener 32 relative to second arm 36 in one direction. First flange 170 defines a first groove 178 extending between outer surface 144 and first flange 170 and second flange 172 defines a second groove 180 extending between outer surface 144 and second flange 172. First and second grooves 178, 180 are each configured for disposal of at least a portion of bone fastener 32 to engage second arm 36 with bone fastener 32 and prevent rotation of bone fastener 32 relative to second arm 36 about second longitudinal axis a2.

First extension 140 includes an inner surface 182 defining longitudinal cavity 184 configured for axial translation of second extension 142 therein. First extension 140 includes oblong openings, circular openings and rails, similar to first extension 40 described above.

Proximal end 151 is configured for engagement with at least a portion of an actuator 204 to prevent axial translation of second extension 142 within longitudinal cavity 184. Second portion 202 includes a planar end wall 206 extending between planar sidewalls 208. Proximal end 151 of first extension 140 includes a transverse groove 210 extending transverse to second longitudinal axis a2 through convex portion 148 configured to allow for the attachment of other instruments, such as, for example, drivers and reducers.

Second extension 142 is configured for axial translation within longitudinal cavity 184 and includes a cavity 212 configured for moveable disposal of ramp 164 extending between a first stop 214 engageable ramp 164 to define a first moveable limit of second extension 142 and a second stop 216 engageable with ramp 164 to define a second moveable limit of second extension 142 along second longitudinal axis a2. First and second stops 214, 216 are planar and extend between planar side surfaces. Second extension 142 is substantially rectangular and includes planar sidewalls 218 extending between a planar distal face 220 and a proximal end 222 having a curved protrusion 224 extending perpendicularly from second extension 142 including an eyelet 226 extending transverse to second longitudinal axis a2 through protrusion 224. Second extension 142 has a width w2, which is less than a width of longitudinal cavity 184 such that second extension 142 can translate axially within longitudinal cavity 184. Width w2 of second extension 142 is greater than a width w3 of extension retaining portion 147 such that extension retaining portion 147 and rails 87 retain second extension 142 within longitudinal cavity 184.

Second extension 142 may be advanced proximally within longitudinal cavity 184 such that a distal end of second extension 142 moves from distal end 168 to proximal end 166 of ramp 164. Second surface 192 extends beyond outer surface 144 as the distal end of second extension 142 is advanced proximally over ramp 164. Second extension 142 may be moved proximally within longitudinal cavity 184 until proximal end 166 of ramp 164 engages first stop 214 to prevent second extension 142 from further advancing proximally within longitudinal cavity 184. Ramp 164 engages first stop 214 such that second arm 36 is disposed in a first configuration such that second surface 192 of projection 154 extends beyond outer surface 144 of first extension 140.

Second extension 142 may be advanced distally within longitudinal cavity 184 such that the distal end of second extension 142 moves from proximal end 168 to distal end 168 of ramp 164, to move second arm 36 from the first configuration to a second configuration. Second surface 192 moves inwardly as the distal end of second extension 142 is advanced distally over ramp 164 such that ramp 164 recesses and/or is disposed within cavity 212. Second surface 192 is disposed into alignment with outer surface 144. Second extension 142 may be advanced distally within longitudinal cavity 184 until distal end 168 engages second stop 216 and distal face 220 is disposed within undercut 194 to prevent second extension 138 from further advancing distally within longitudinal cavity 184. Ramp 164 engages second stop 216 and second arm 36 is disposed in the second configuration such that second surface 192 of projection 154 is aligned with outer surface 144.

Actuator 204 includes a body portion 228 configured to moveably engage at least a portion of proximal end 151. Actuator 204 includes a locking element 230 having a circular opening 232 extending transverse to second longitudinal axis a2 through locking element 230. A cylindrical pin 234 is inserted through eyelet 226 in second extension 142 and opening 232 in locking element 230 when second extension 142 is retained within longitudinal cavity 184 such that locking element 230 is pivotable relative to first and second extensions 140, 142. Axial translation of actuator 204 causes axial translation of second extension 142 within longitudinal cavity 184. Locking element 230 includes a first end 236 having a planar face extending between planar sidewalls and is configured for disposal within second portion 202 of first extension 140 to prevent axial translation of second extension 142 within longitudinal cavity 184. Locking element 230 is biased into engagement with second portion 202 of first extension 140 via a spring (not shown) positioned between first end 236 of locking member 230 and body portion 228. A depressible tab 238 positioned at a second end of locking element 236, opposite first end 236. Depressible tab 238 is pivotable about pin 234 such that advancing depressible tab 238 in one direction moves first end 236 of activator 204 in an opposite direction such that first end is removed from second portion 202 of first extension 140 which disengages locking element 230 from first extension 140.

Bone fastener 32 includes a proximal portion, such as, for example, a receiver 254 having a pair of spaced apart arms 256, 258 extending parallel to first longitudinal axis a1 and second longitudinal axis a2 that define an implant cavity 260 and a distal portion, such as, for example, a shaft 262 configured for penetrating tissue. Each arm 256, 258 includes an outer surface 264 and first and second side surfaces 266, 268 each having a longitudinal groove 270 extending parallel to first longitudinal axis a1 and second longitudinal axis a2 configured to engage first flange 70, 170 or second flange 72, 172 of first extensions 38, 140 to retain extender 30 with bone fastener 32 and prevent rotation of extender 30 relative to bone fastener 32. Outer surface 264 of each arm 256, 258 includes a longitudinal channel 272 extending parallel to first longitudinal axis a1 and second longitudinal axis a2 having a size and shape corresponding to that of tips 60, 160, such as, for example, arrowhead shaped, configured for disposal of tips 60, 160. Concave portions 44, 146 of first extensions 38, 140 define an implant cavity 265 configured for axial translation of an implant therethrough. Implant cavity 265 is in communication with implant cavity 260 such that an implant can be advanced distally through implant cavity 265 for disposal in implant cavity 260. It is contemplated that arm 256 and/or arm 258 may be disposed at alternate orientations, relative to first longitudinal axis a1 or second longitudinal axis a2, such as, for example, transverse, perpendicular and/or other angular orientations such as acute or obtuse, co-axial and/or may be offset or staggered. It is envisioned that all or only a portion of longitudinal channels 272 may be variously configured and dimensioned, such as, for example, round, oval, oblong, square, rectangular, polygonal, irregular, uniform, non-uniform, offset, staggered, tapered, consistent or variable, depending on the requirements of a particular application.

At least a portion of an inner surface of receiver 254 is threaded and engageable with a coupling member, such as, for example, a setscrew. It is envisioned that the inner surface of receiver 254 can include a thread form located adjacent arm 256 and a thread form located adjacent arm 258 each configured for engagement with a setscrew. It is envisioned that the inner surface of receiver 254 may be disposed with the setscrew in alternate fixation configurations, such as, for example, friction fit, pressure fit, locking protrusion/recess, locking keyway and/or adhesive. It is contemplated that all or only a portion of the inner surface of receiver 254 may have alternate surface configurations to enhance fixation with the setscrew such as, for example, rough, arcuate, undulating, mesh, porous, semi-porous, dimpled and/or textured according to the requirements of a particular application.

Shaft 262 is threaded along a length thereof and has a cylindrical cross section configuration and includes an outer surface having an external thread form. It is contemplated that the thread form may include a single thread turn or a plurality of discrete threads. It is further contemplated that other engaging structures may be located on shaft 262, such as, for example, a nail configuration, barbs, expanding elements, raised elements and/or spikes to facilitate engagement of shaft 40 with tissue, such as, for example, vertebrae and/or iliac bone. It is envisioned that all or only a portion of shaft 262 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 262 may include one or a plurality of openings. It is further contemplated that all or only a portion of the outer surface of shaft 262 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 262 may be disposed at various orientations, relative to axis a, such as, for example, transverse, perpendicular and/or other angular orientations such as acute or obtuse and/or may be offset or staggered. It is further envisioned that all or only a portion of shaft 262 may be cannulated.

Projections 54, 154 are transversely moveable between the first configuration, discussed above, such that projections 54, 154 extend beyond outer surfaces 42, 144 and the second configuration, discussed above, whereby second extensions 40, 142 axially translate within the respective longitudinal cavity 84, 184 and engage the respective ramp 64, 164 such that projections 54, 154 are disposed in alignment with outer surfaces 42, 144 and tips 60, 160 are disposed within longitudinal channels 272 such that locking elements 130, 230 engage proximal portion 254 of bone fastener 32.

In operation, first and second grooves 78, 80 of first extension 38 are aligned with longitudinal grooves 270 in arm 256 of bone fastener 32 such that first and second flanges 70, 72 engage side surfaces 268, 270 to engage bone fastener 32 with first arm 34 and prevent rotation of first arm 34 relative to bone fastener 32. First and second grooves 178, 180 are aligned with longitudinal grooves 270 such that first and second flanges 170, 172 engage side surfaces 268, 270 to engage bone fastener 32 with second arm 36 and prevent rotation of second arm 36 relative to bone fastener 32. Second extensions 40, 142 are disposed in longitudinal cavities 84, 184 for axial translation therein. Second extensions 40, 142 are advanced proximally within longitudinal cavities 84, 184 such that the distal ends of second extensions 40, 142 move from distal ends 68, 168 of ramps 64, 164 to proximal ends 66, 166. Second surfaces 92, 192 extend beyond outer surfaces 42, 144 as the distal ends of second extensions 40, 142 are advanced proximally over ramps 64, 164. Second extensions 40, 142 may be moved proximally within longitudinal cavities 84, 184 until proximal ends 66, 166 engages first stops 114, 214 to prevent second extensions 40, 142 from further advancing proximally within longitudinal cavities 84, 184. Ramps 64, 164 engage first stops 114, 214 and arms 34, 36 are disposed in a first configuration such that second surfaces 92, 192 extend beyond outer surfaces 42, 144, as shown in FIG. 17.

Second extensions 40, 142 are advanced distally within longitudinal cavities 84, 184 such that the distal ends of second extensions 40, 142 move from proximal ends 68, 168 of ramps 64, 164 to distal ends 68, 168 to move arms 34, 36 from the first configuration to a second configuration. Second surfaces 92, 192 move inwardly as the distal ends of second extensions 40, 142 are advanced distally over ramps 64, 164 and ramps 64, 164 recess and/or are disposed within cavities 112, 212, respectively. Second surfaces 92, 192 are disposed into alignment with outer surfaces 42, 144. Second extensions 40, 142 may be advanced distally within longitudinal cavities 84, 184 until distal ends 68, 168 engage second stops 116, 216 and distal faces 120, 220 are disposed within undercuts 94, 194 to prevent second extensions 40, 142 from further advancing distally within longitudinal cavities 84, 184. Ramps 64, 164 engage second stops 116, 216 and arms 34, 36 are disposed in the second configuration such that second surfaces 92, 192 are aligned with outer surfaces 42, 144, as shown in FIG. 18.

Figure 19:
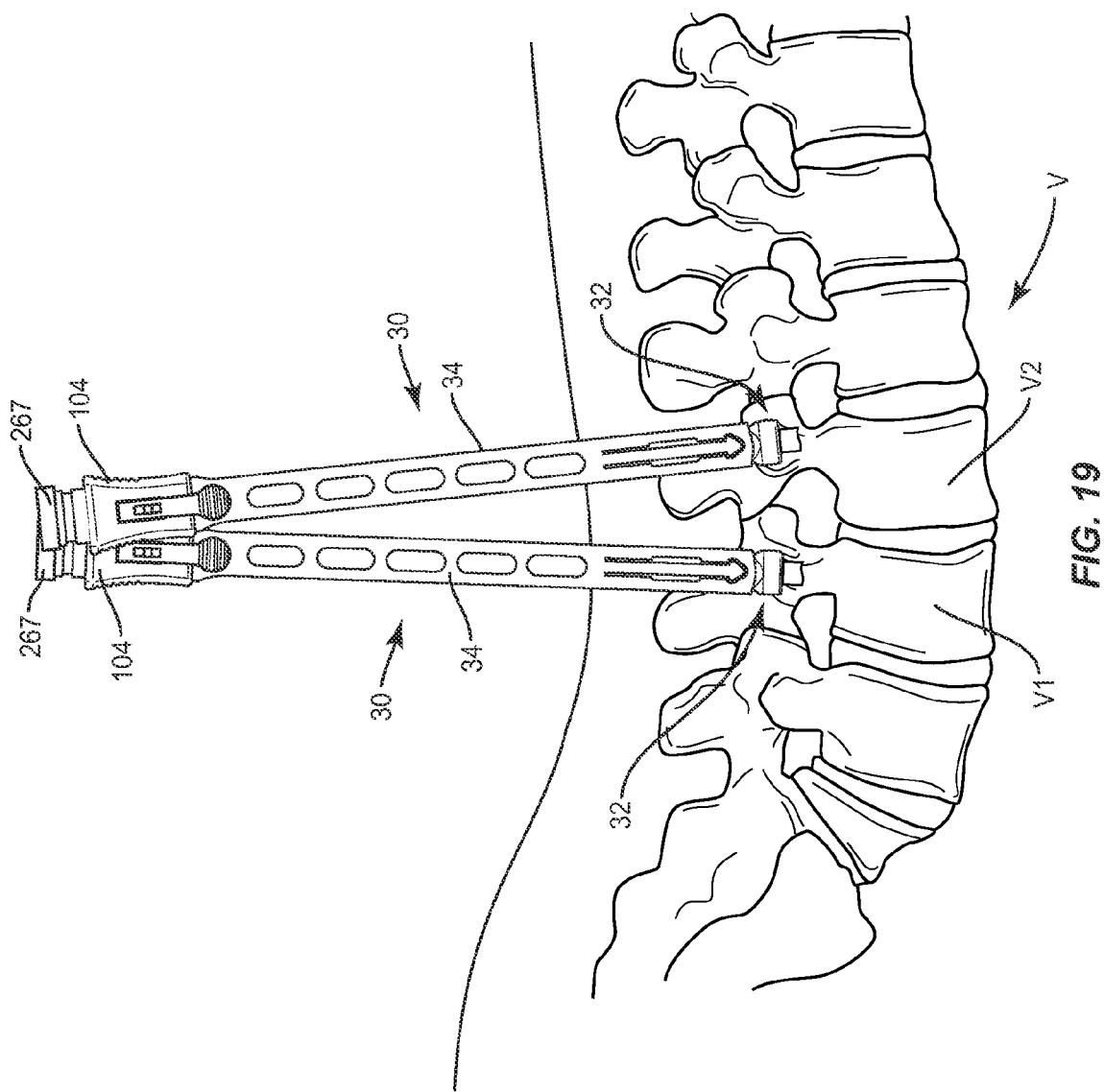
FIG. 19 is a plan view of one embodiment of a system in accordance with the principles of the present disclosure disposed with vertebrae.

In use, as shown in FIG. 19, to treat the affected section of vertebrae V, a medical practitioner obtains access to a surgical site including vertebrae V1, V2 in any appropriate manner, such as through incision and refraction of tissues. It is envisioned that the spinal implant system may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. The spinal implant system is then employed to augment the surgical treatment. The spinal implant system can be delivered or implanted as a pre-assembled device or can be assembled in situ. The components of the spinal implant system may be completely or partially revised, removed or replaced during or after the surgical procedure.

Pilot holes or the like are made in vertebrae V1, V2 for receiving shaft 262 of bone fastener 32. The spinal implant system is disposed adjacent vertebrae V at a surgical site and the components of spinal implant system are manipulable to drive, torque, insert or otherwise connect bone fastener 32 to vertebrae, according to the particular requirements of the surgical treatment.

Initially, extender 30 is disposed in the first configuration (FIG. 17), described above, such that projections 54, 154 extend beyond outer surfaces 42, 144. To provisionally capture bone fastener 32, extender 30 is positioned relative to bone fastener 32 such that projections 54, 154 are aligned with longitudinal channels 272. Second extensions 40, 142 are advanced distally within longitudinal cavities 84, 184 via actuators 104, 204. Second surfaces 92, 192 are brought into alignment with outer surfaces 42, 144 as the distal ends of second extensions 40, 142 are advanced distally over ramps 64, 164.

Second surfaces 92, 192 are aligned with outer surfaces 42, 144 and tips 60, 160 engage channels 272 for disposal therein to engage extender 30 with bone fastener 32, in the second configuration (FIG. 18). A spacer 267 is positioned between first and second arms 34, 36 to connect arms 34, 36. Spacer 267 includes an opening configured to passage of instruments (not shown), such as, for example, a driver for applying torque and driving bone fastener 32 into vertebra V1, V2 and/or a rod reduction instrument such that the instrument may be passed through the opening in spacer 267 and into implant cavity 265. Upon treatment employing the components of the spinal implant system, bone fastener 32 is ejected from extender 30 for fixation with vertebrae V1, V2.

To eject extender 30 from bone fastener 32, the medical practitioner advances second extensions 40, 142 proximally within longitudinal cavities 84, 184 via actuators 104, 204. Second surfaces 92, 192 move outwardly as the distal ends of second extensions 40, 142 are advanced proximally over ramps 64, 164 such that tips 60, 160 of projections 54, 154 are removed from longitudinal channels 272. Extender 30 is released from engagement with bone fastener 22 such that projections 54, 154 disengage longitudinal channels 272 and bone fastener 32 is fixed securely with V1, V2. Upon completion of the procedure, the surgical instruments and assemblies are removed from the surgical site and the incision is closed.

Bone fastener 32 may be employed as a bone screw, pedicle screw, or multi-axial screw used in spinal surgery. It is contemplated that bone fastener 32 may be coated with an osteoconductive material such as hydroxyapatite and/or osteoinductive agent such as a bone morphogenic protein for enhanced bony fixation. Bone fastener 32 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

It is envisioned that the spinal implant system may include one or a plurality of extenders, inserters, reducers, bone fasteners and/or vertebral constructs, which may be alternately sized and dimensioned, and arranged as a kit, according to the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An extender comprising:
   a first arm defining a first longitudinal axis and including a first extension and a second extension,
   the first extension including an outer surface and a projection extending from the outer surface, the projection including a ramp and a first locking element, the first extension including an inner surface defining a longitudinal cavity, and
   an actuator configured to cause axial translation of the second extension within the longitudinal cavity, wherein a cylindrical in is inserted through an eyelet in the second extension and an opening in a locking element of the actuator such that the locking element is pivotable relative to the first and second extensions,
   wherein the projection is transversely moveable between a first configuration such that the projection extends beyond the outer surface and a second configuration whereby the second extension axially translates within the longitudinal cavity and engages the ramp such that the projection is disposed in alignment with the outer surface and the first locking element engages an implant.

2. An extender as recited in claim 1, further comprising a second arm including a second locking element that engages the implant.

3. An extender as recited in claim 1, further comprising a second arm including a first extension and a second extension, the first extension of the second arm including an outer surface and a projection extending therefrom, the projection of the second arm including a ramp and a second locking element, the first extension of the second arm including an inner surface defining a longitudinal cavity, the projection of the second arm being transversely moveable between the first configuration and the second configuration such that the second locking element engages the implant.

4. An extender as recited in claim 1, further comprising a second arm including an outer surface having a concave portion and the outer surface of the first arm having a concave portion, the concave portions defining an implant cavity.

5. An extender as recited in claim 1, wherein the projection pivots relative to the outer surface.

6. An extender as recited in claim 1, wherein the first locking element comprises a pointed tip and a flange configured to engage the implant.

7. An extender as recited in claim 1, wherein the ramp is tapered between a proximal end having a first height and a distal end having a second, decreased height, the distal end being closer to a tip of the first locking element than the distal end.

8. An extender as recited in claim 1, wherein the second extension includes a first stop engageable with the ramp to define a first moveable limit of the second extension and a second stop engageable with the ramp to define a second moveable limit of the second extension along the first longitudinal axis.

9. An extender as recited in claim 1, wherein a distal end of the first extension includes a first flange and a second flange, the flanges being configured for capture of the implant.

10. An extender as recited in claim 1, wherein the implant includes a bone fastener.

11. An extender as recited in claim 1, wherein a distal end of the first extension includes a flange extending transverse to the first longitudinal axis and being configured to engage the implant.

12. An extender as recited in claim 1, wherein the locking element of the actuator is engageable with the first extension and being configured to fix the second extension in the second configuration.

13. An extender as recited in claim 12, wherein the locking element of the actuator is biased into engagement with the first extension.

14. An extender as recited in claim 12, wherein the actuator includes a depressible tab configured to disengage the locking element of the actuator from the first extension.

15. An extender as recited in claim 1, wherein the ramp extends through a cavity in the second extension as the projection moves between the first and second configurations.

16. An extender as recited in claim 1, wherein the first extension comprises a concave portion and a convex portion opposite the concave portion, the concave portion comprising a plurality of rails each extending between side surfaces of the first extension, the rails being configured to retain at least a portion of the second extension within the longitudinal cavity.

17. An extender comprising:
   a first arm defining a first longitudinal axis and including a first extension and a second extension,
   the first extension including an outer surface and a projection extending from the outer surface, the projection including a ramp and a first locking element, the first extension including an inner surface defining a longitudinal cavity, and an actuator configured to cause axial translation of the second extension within the longitudinal cavity, wherein a cylindrical pin is inserted through an eyelet in the second extension and an opening in a locking element of the actuator such that the locking element is pivotable relative to the first and second extensions, wherein the projection is transversely moveable between a first configuration such that the projection extends beyond the outer surface and a second configuration whereby the second extension axially translates within the longitudinal cavity and engages the ramp such that the projection is disposed in alignment with the outer surface and the first locking element engages an implant, wherein the ramp extends through a cavity in the second extension as the projection moves between the first and second configurations.

18. An extender comprising:

a first arm defining a first longitudinal axis and including a first extension and a second extension, the first extension including an outer surface and a projection extending from the outer surface, the projection including a ramp and a first locking element, the first extension including an inner surface defining a longitudinal cavity, wherein the projection is transversely moveable between a first configuration such that the projection extends beyond the outer surface and a second configuration whereby the second extension axially translates within the longitudinal cavity and engages the ramp such that the projection is disposed in alignment with the outer surface and the first locking element engages an implant, wherein the second extension includes a first stop engageable with the ramp to define a first moveable limit of the second extension and a second stop engageable with the ramp to define a second moveable limit of the second extension along the first longitudinal axis, and wherein the limits define a cavity therebetween configured for moveable disposal of the ramp.

* * * * *

UNITED STATES PATENT AND TRADEMARK OFFICE
CERTIFICATE OF CORRECTION

PATENT NO. : 9,220,539 B2  
APPLICATION NO. : 13/424048  
DATED : December 29, 2015  
INVENTOR(S) : McBride et al.

It is certified that error appears in the above-identified patent and that said Letters Patent is hereby corrected as shown below:

Specification

In Column 14, Line 30, delete "refraction" and insert -- retraction --, therefor.

Claims

In Column 15, Line 54, in Claim 1, delete "in is" and insert -- pin is --, therefor.

Signed and Sealed this
Tenth Day of May, 2016

Michelle K. Lee
*Director of the United States Patent and Trademark Office*